Figure 1:
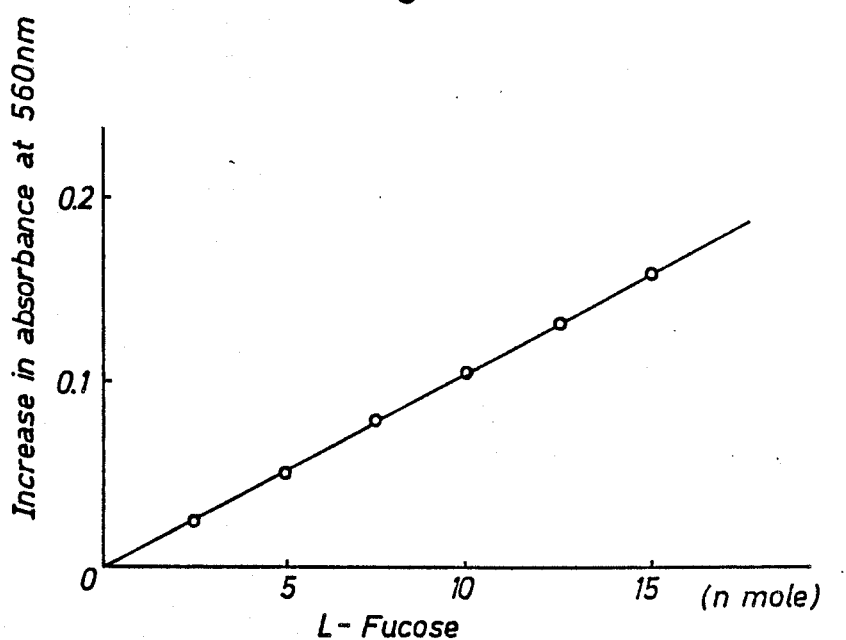

| United States Patent [19] | [11] Patent Number: 4,927,753 |
| Sakai et al. | [45] Date of Patent: May 22, 1990 |

[54] QUANTITATIVE DETERMINATION OF L-FUCOSE

[75] Inventors: Takeshi Sakai; Susumu Matsui, both of Shiga; Sumiko Akiyoshi, Kyoto; Akira Obayashi, Uji, all of Japan

[73] Assignee: Takara Shuzo Co., Ltd., Kyoto, Japan

[21] Appl. No.: 3,283

[22] Filed: Jan. 14, 1987

[30] Foreign Application Priority Data

Jan. 29, 1986 [JP] Japan ................................. 61-17435

[51] Int. Cl.$^5$ .......................... C12Q 1/32; C12Q 1/34; C12N 9/04; C12R 1/15
[52] U.S. Cl. ........................................ 435/26; 435/18; 435/190; 435/843
[58] Field of Search ................... 435/26, 18, 190, 843, 435/810

[56] References Cited

PUBLICATIONS

Schachter et al., Journal of Biological Chemistry, vol. 244, No. 17, Sep. 10, 1969, pp. 4785–4792.

Barman, Enzyme Handbook, Supplement I, Springer-Verlag, New York, (1974) p. 48.

*Primary Examiner*—Randall E. Deck
*Attorney, Agent, or Firm*—Wenderoth, Lind & Ponack

[57] ABSTRACT

A method is provided for the quantitative determination of L-fucose in a sample solution. According to the method an L-fucose dehydrogenase having its optimum pH around neutrality is allowed to act upon the sample solution in the presence or absence of an α-L-fucosidase, and the amount of reduced nicotinamide adenine dinucleotide thus formed is measured.

5 Claims, 2 Drawing Sheets

QUANTITATIVE DETERMINATION OF L-FUCOSE

This invention relates to a method for the quantitative determination for L-fucose in sample solutions by use of L-fucose dehydrogenase having its optimum pH around neutrality.

The α-L-fucosyl groups attached to the nonreducing terminals or branches of complex glycochains derived from higher animals play an important role in cell recognition and immunoresponse. For example, this group serves as an antigenic determinant in the ABO and Lewis blood groups, and studies on the relationship between the glycochain structure of the blood-group substances and antigenic specificity have been receiving special attention in recent years. Furthermore, malignant changes of cells are reflected in marked changes in the glycochains on glycolipids involved, and the tumor-related glycolipids are, in many cases, those in which changes have occurred at the nonreducing terminals of the glycochains inherent to the affected tissue—a phenomenon closely related to differentiation of tissues. This means that cancer of an internal organ is accompanied by the accumulation of L-fucose-containing glycolipid specific to that organ. Since these cancer-related glycochain antigens are also released into the blood, structural analysis of glycochain antigens in the blood is used for the diagnosis of internal-organ cancers. α-L-fucosidase, an enzyme which acts upon the α-L-fucosyl group in complex glycolipids to libererate L-fucose, is effective for the analysis of the location of this group on various glycochains. The degree of malignant change can be estimated if the L-fucose contained is released by the action of this enzyme or by chemical treatment at 100° C. for one hour in the presence of 0.1N trichloroacetic acid, follwed by quantitative determination of the released L-fucose. The content of L-fucose in the blood is being adopted as an index for the degree of malignant change, because it decreases with the progress of cancer and increases as the cancer retrogrades as a result of chemotherapy.

Various methods are known for the quantitative determination of L-fucose. These include a process in which a fraction containing free L-fucose is obtained from sample solutions by gel filtration or ion-exchange technique, followed by determination by gas chromatography [Methods in Enzymology, 28, 738 (1972)]; and a process which quantitatively determines acetaldehyde formed by periodate oxidation of L-fucose [Journal of Biological Chemistry, 245, 1659 (1970)]. These chemical processes are very cumbersome in operation and also unsatisfactory in measurement accuracy. The enzymatic method using an L-fucose dehydrogenase, on the other hand, ensures rapid and correct determination of L-fucose with no need for its isolation from sample solutions. But this enzymatic method also suffers from some problems as explained below. L-Fucose dehydrogenase has been reported to be present in the cells of *Pullularia pullulans* and in the liver of pigs and rabbits. This enzyme, whether it be of the microbial or animal origin, has an optimum reaction pH at near 10, which is not desirable in that effective determination of L-fucose cannot be achieved without damaging living cells. In addition, the above-mentioned α-L-fucosidase has its optimum reaction pH in the acidic or weakly acidic region, and exerts little action at a pH near 10. Hence, it has been impracticable to determine L-fucose in a complex glycochain in one step by the action of α-L-fucosidase and L-fucose dehydrogenase; instead, a more intricate procedure has to be followed, in which α-L-fucosidase is first allowed to act upon a sample solution in the acidic or weakly acidic region to release L-fucose, the reaction mixture is then alkalified, and L-fucose dehydrogenase is allowed to act for the quantitative determination of L-fucose.

The object of this invention is to provide a rapid, simple and low-cost method for the quantitative determination of L-fucose which employs an L-fucose dehydrogenase having its optimum reaction pH around neutrality.

Assiduous studies in search of such a quantitative method have led us to find that this object can be achieved by the use of a specific L-fucose dehydrogenase.

Briefly, this invention relates to a method for the quantitative determination of L-fucose which comprises allowing an L-fucose dehydrogenase having its optimum reaction pH around neutrality to act upon a sample solution in the presence or absence of an α-L-fucosidase, measuring the amount of reduced nicotinamide adenine dinucleotide thus formed and relating the amount of reduced nicotinamide adenine dinucleotide measured to the amount of L-fucose in the sample.

The method of this invention is characterized in that a specific L-fucose dehydrogenase having its optimum reaction pH around neutrality is used for the quantitative determination of L-fucose, and in that the quantitative determination of L-fucose using such a specific L-fucose dehydrogenase is carried out in the presence of nicotinamide adenine dinucleotide (NAD), followed by measurement of the increase in ultraviolet absorbance of reduced nicotinamide adenine dinucleotide (NADH), or in the presence of NAD, a tetrazolium salt (oxidized form), and diaphorase or phenazine methosulfate (oxidized form), followed by determination of the formazan dye formed.

Sample solutions containing free L-fucose and/or L-fucose bonded to specimens from the body may be applicable to the method of this invention. The l-fucose in the sample solution may be free L-fucose and/or L-fucose bonded to the glucoconjugates on the surface of cells or glycoconjugates.

Any L-fucose dehydrogenase having an optimum reaction pH around neutrality may be used for the method of this invention. A typical example is the enzyme produced by the culture of Corynebacterium sp. FS-0077 (FERM BP-1234).

Shown below are the properties of L-fucose dehydrogenase which may be used in the method of this invention.

(1) Action

This enzyme oxidizes L-fucose into L-fucono-δ-lactone as shown in the following reaction formula:

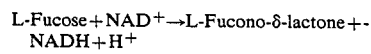

(2) Optimum pH

The optimum pH for this enzyme is in the range of about 7.5 to 8.0.

Measurement of Enzyme Activity:

A mixture of 1.0 ml of 30 mM L-fucose, 1.8 ml of 200 mM glycine-NaOH buffer solution (pH 8.0), 0.1 ml of 15 mM NAD and 0.1 ml of enzyme solution with a proper concentration (a total of 3.0 ml) was allowed to stand at 37° C. for 10 minutes, and the absorbance of the resulting solution at 340 nm was measured ($OD_{sample}$). Separately, a similar mixture using 0.1 ml distilled water in place of the enzyme solution was prepared and treated in the same manner as above, and the absorbance at 340 nm was measured likewise ($OD_{blank}$). $\Delta OD_{340}$ ($OD_{sample} - OD_{blank}$) was calculated and the activity of L-fucose dehydrogenase determined from the following equation:

$$\text{Units/ml} = \frac{\Delta OD \times 3.0(\text{ml})}{6.22 \times 10(\text{min}) \times 0.1.(\text{ml}) \times d} \times df$$

6.22: Molecular extinction coefficient of NADH at 340 nm
d: Optical path length (cm)
df: Dilution factor Action of the L-fucose dehydrogenase upon L-fucose in the presence of NAD gives L-fucono-δ-lactone and NADH. Any known method can be used for the determination of NADH: for example, measuring the molecular extinction coefficient of NADH itself at 340 nm; or allowing a tetrazolium salt (such as Nitroblue-tetrazolium and Indonitro-tetrazolium) (oxidized form), and diaphorase or phenazine methosulfate (oxidized form), to act upon NADH, followed by measurement of the absorbance of formazan dye thus formed at 540 to 580 nm.

When analyzing L-fucose bonded to specimens from the body, free L-fucose is first released by the action of α-L-fucosidase upon the sample solution or by chemical treatment, for example, with 0.1N trichloroacetic acid at 100° C. for one hour, and L-fucose dehydrogenase is then allowed to act upon the free L-fucose, followed by quantitative determination of NADH thus formed by the method described above.

Any α-L-fucosidase derived from microorganisms (such as species belonging to the genera Aspergillus, Clostridium and Fusarium) and from fish and shellfish (such as *Turbo cornutus* and *Charonia lampus*) may be used for the purpose of this invention. But, since these have optimum pH in the acidic or weakly acidic region, use of α-L-fucosidase from Corynebacterium sp. FS-0077 (FERM BP-1234), having its optimum pH around neutrality, is most advantageous.

There is no specific limitation upon the type of buffer solution used in the method of this invention. Phosphate, Tris, glycine and Good's buffers may be advantageously used, with the preferable pH range being from 6 to 10 (most preferably from 7.5 to 8.5).

The L-fucose dehydrogenase is preferably used in an amount of 0.2 to 20 units, most preferably 1 to 5 units, while diaphorase is preferably employed in an amount of 0.5 to 20 units, most preferably 1 to 5 units. When analyzing free L-fucose, the amounts of tetrazolium salt (oxidized form) and NAD to be used should be at least equimolar to that of L-fucose. When α-L-fucosidase is used to release bonded L-fucose, it should be used in an amount of 1 to 50 units (preferably 5 units), and the reaction should preferably be carried out at 20° to 40° C. for 2 to 20 minutes. In this case, the sample solution may also contain L-fucose dehdyrogenase, tetrazolium salt (oxidized form), and diaphorase or phenazine methosulfate (oxidized form).

The method for the quantitative determination of L-fucose described above may be summarized in the following reaction formulas:

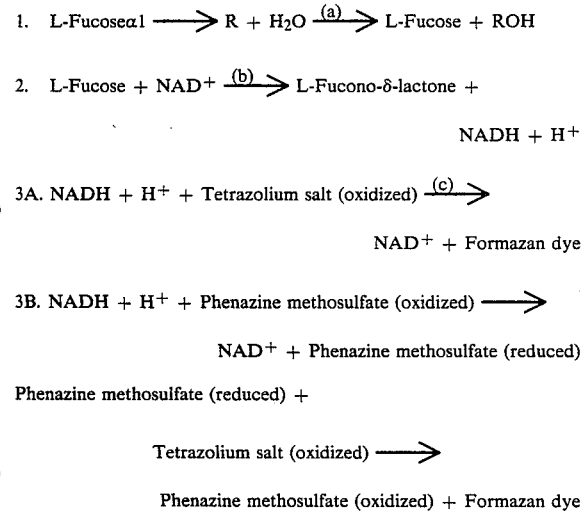

(a): α-L-Fucosidase
(b): L-Fucose dehydrogenase
(c): Diaphorase

As may be apparent from the foregoing, this invention provides a new method for colorimetric determination of L-fucose useful in clinical testing, which is very simple, highly sensitive, and specific. In addition, the L-fucose dehydrogenase used in the method of this invention can be obtained in large quantities from microorganisms at a low cost.

Figure 2:
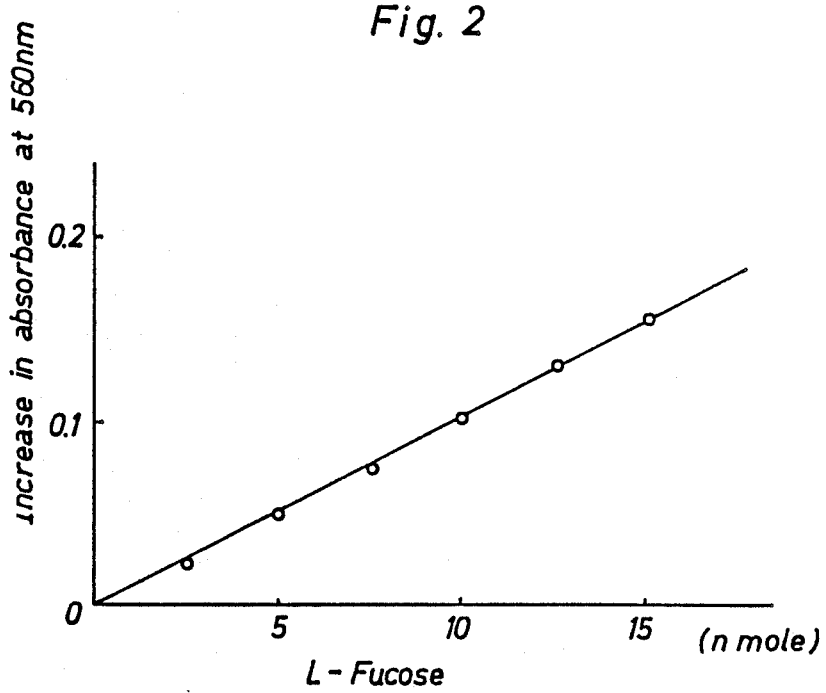
Figure 3:
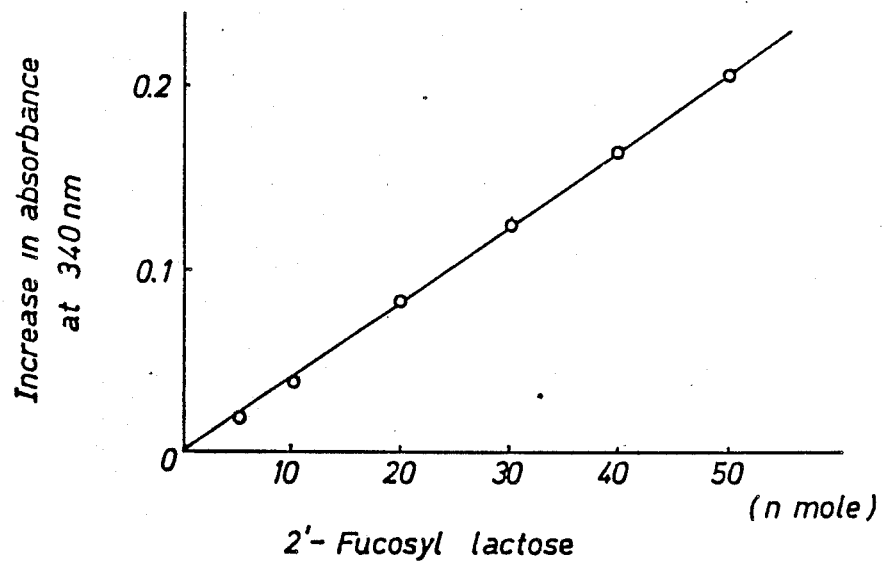
Figure 4:
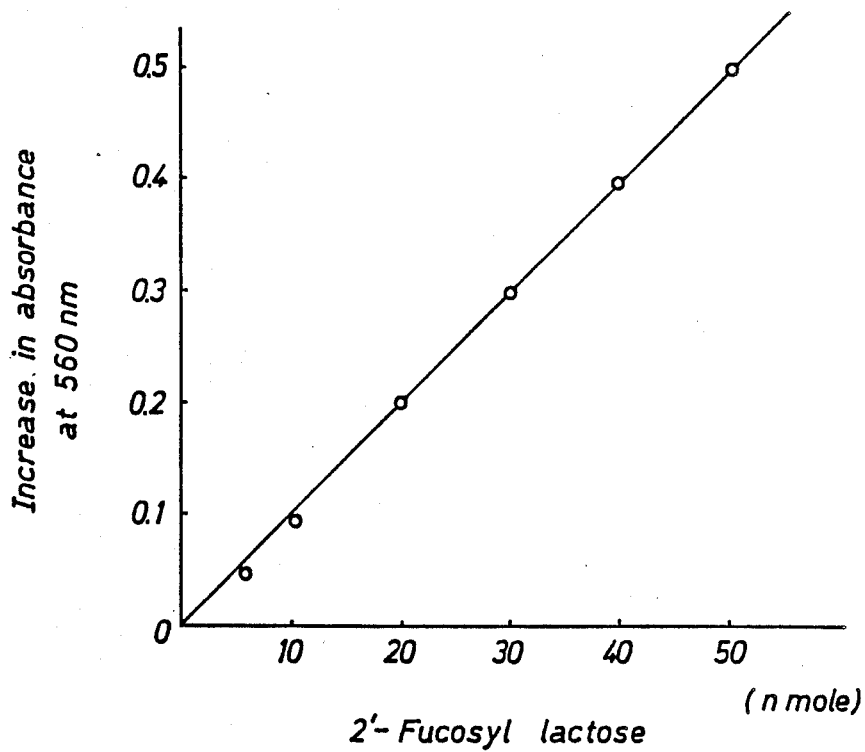

The invention will be further explained by the following non-limitative examples and also by referring to the accompanying drawings wherein: FIG. 1 is a calibration curve of Example 1 showing the relationship between the amount of L-fucose used and the difference in absorbance at 560 nm; FIG. 2 is a calibration curve of Example 2 showing the relationship between the amount of L-fucose used and the difference in absorbance at 560 nm; FIG. 3 is a calibration curve of Example 3 showing the relationship between the amount of 2'-fucosyl-lactose used and the difference in absorbance at 340 nm; and FIG. 4 is a calibration curve of Example 4 showing the relationship between the amount of 2'-fucosyl-lactose used and the difference in absorbance at 560 nm.

EXAMPLE 1

Determination of L-fucose

| | | |
|---|---|---|
| 200 mM | Glycine/NaOH buffer (pH 8.5) | 0.8 ml |
| 15 mM | NAD$^+$ | 0.1 ml |
| 20 units/ml | L-Fucose dehydrogenase | 0.1 ml |
| 20 units/ml | Diaphorase (from Clostridium; Toyobo Co., Ltd.) | 0.1 ml |
| 1.2 mM | Nitroblue tetrazolium (oxidized form) | 0.1 ml |
| | Water | 0.2 ml |

To the above mixture (a total of 1.4 ml) was added 0.1 ml of L-fucose solution (0, 0.025, 0.05, 0.075, 0.1, 0.125 and 0.15 mM concentrations), each of the resulting solutions was allowed to stand at 37° C. for 10 minutes, and the absorbance at 560 nm was measured. As shown in FIG. 1, a good linear relationship was observed between the amount of L-fucose used and the increase in absorbance at 560 nm.

EXAMPLE 2

Determination of L-fucose

| 100 mM | Phosphate buffer (pH 8.5) | 1.0 ml |
| --- | --- | --- |
| 15 mM | NAD+ | 0.1 ml |
| 20 units/ml | L-Fucose dehydrogenase | 0.1 ml |
| 30 μM | Phenazine methosulfate | 0.1 ml |
| 1.2 mM | Nitroblue tetrazolium (oxidized form) | 0.1 ml |

To the above mixture (a total of 1.4 ml) was added 0.1 ml of L-fucose solution (0, 0.025, 0.05, 0.075, 0.1, 0.125 and 0.15 mM concentrations), each of the resulting solutions was allowed to stand at 37° C. for 10 minutes, and the absorbance at 560 nm was measured. As shown in FIG. 2, a good linear relationship was observed between the amount of L-fucose used and the increase in absorbance at 560 nm.

EXAMPLE 3

Determination of L-fucose in 2'-fucosyl-lactose

| 100 mM | Phosphate buffer (pH 8.5) | 1.1 ml |
| --- | --- | --- |
| 15 mM | NAD+ | 0.1 ml |
| 20 units/ml | L-Fucose dehydrogenase | 0.1 ml |
| 50 units/ml | α-L-Fucosidase (from Corynebacterium; Takara Shuzo Co. Ltd.) | 0.1 ml |

To the above mixture (a total of 1.4 ml) was added 0.1 ml solution of 2'-fucosyl-lactose from human milk (0, 0.05, 0.1, 0.2, 0.3, 0.4 and 0.5 mM concentrations), and each of the resulting solutions was allowed to stand at 37° C. for 10 minutes. As shown in FIG. 3, a good linear relationship was observed between the amount of L-fucosyl-lactose used and the increase in absorbance at 340 nm.

EXAMPLE 4

Determination of L-fucose in 2'-fucosyl-lactose

| 100 mM | Phosphate buffer (pH 8.5) | 0.9 ml |
| --- | --- | --- |
| 15 mM | NAD+ | 0.1 ml |
| 20 units/ml | L-Fucose dehydrogenase | 0.1 ml |
| 50 units/ml | α-L-Fucosidase (from Corynebacterium; Takara Shuzo Co. Ltd.) | 0.1 ml |
| 20 units/ml | Diaphorase (from Clostridium; Toyobo Co., Ltd.) | 0.1 ml |
| 1.2 mM | Nitroblue tetrazolium (oxidized form) | 0.1 ml |

To the above mixture (a total of 1.4 ml) was added 0.1 ml solution of 2'-fucosyl-lactose from human milk (0, 0.05, 0.1, 0.2, 0.3, 0.4 and 0.5 mM concentrations), and each of the resulting solutions was allowed to stand at 37° C. for 10 minutes. As shown in FIG. 4, a good linear relationship was observed between the amount of 2'-fucosyl-lactose used and the increase in absorbance at 560 nm.

As detailed above, the method of this invention allows quantitative determination of L-fucose more rapidly and simply at lower costs than conventional methods, and hence is of great use in clinical testing.

The following Reference Examples describe the manufacturing processes of L-fucose dehydrogenase and α-L-fucosidase which may be used in the practice of the present invention.

REFERENCE EXAMPLE 1

Manufacture of L-fucose dehydrogenase

A culture medium (100 ml) containing 0.5% yeast extract, 1.0% peptone, 0.3% $KH_2PO_4$ and 0.1% $MgSO_4.7H_2O$ (pH 7.0) was placed in a 500-ml conical flask and sterilized at 120° C. for 20 minutes. Corynebacterium sp. FS-0077(FERM BP 1234) was inoculated to this medium and incubated at 30° C. for 24 hours to give a master culture. Separately, a medium (15 liters) containing 0.1% L-fucose, 0.5% peptone, 0.3% $KH_2PO_4$, 0.1% $MgSO_4.7H_2O$ and 0.01%(v/v) of a defoamer (CB-442; Nippon Oils & Fats Co., Ltd.) (pH 7.0) was placed in a 30-l jar fermentor and sterilized at 120° C. for 20 minutes. After cooling, 100 ml of the master culture prepared above was added to the fermentor, and cultivation was continued at 30° C. for 36 hours with aeration (15 liters/min) and agitation (300 rpm). The microbial cells were collected by centrifugation, suspended in 500 ml of a 50 mM phosphate buffer (pH 8.0), and broken down by ultrasonic treatment. The resulting mixture was centrifuged, affording 540 ml of supernatant. Its L-fucose dehydrogenase activity was 37.8 unit/ml. This supernatant was adsorbed on DEAE-Sepharose CL-6B (Pharmacia) packed in a column (5.0 cm in diameter and 10 cm in length) and previously equilibrated with 50 mM phosphate buffer, the column was washed with 100 mM phosphate buffer, and the adsorbed portion was eluted with 300 mM phosphate buffer to collect the active fraction. Sodium chloride was added to the collected fraction so as to give a salt concentration of 4M, and the resulting solution was adsorbed on Phenyl-Sepharose CL-4B (Pharmacia) packed in a column (2.5 cm in diameter and 20 cm in length) and previously equilibrated with 100 mM phosphate buffer containing 4M sodium chloride. The column was washed with 20 mM phosphate buffer containing 3M sodium chloride, and the adsorbed portion was eluted with 20 mM phosphate buffer containing 1M sodium chloride to collect the active fraction. The collected fraction was again adsorbed on Phenyl-Sepharose CL-4B (Pharmacia) packed in a column (2.5 cm in diameter and 10 cm in length), the adsorbed portion was eluted with 50 mM phosphate buffer containing 2M sodium chloride, and the eluate was concentrated through a collodion membrane. The concentrate was subjected to gel filtration through Sepharose CL-6B packed in a column (2.5 cm in diameter and 90 cm in length) and previously equilibrated with 100 mM phosphate buffer, and the active fraction collected was again concentrated, followed by gel filtration through a Sephacryl S-200 packed in a column (2.5 cm in diameter and 100 cm in length; Pharmacia). After addition of EDTA as stabilizer to a final concentration of 1 mM, the filtrate was freeze-dried, affording 820 mg of purified enzyme powder. This powder had a relative activity of 8.41 units/mg and showed a single band when measured by disk electrophoresis on polyacrylamide gel.

REFERENCE EXAMPLE 2

Manufacture of α-L-fucosidase

A culture medium (100 ml) containing 0.5% yeast extract, 1.0% peptone, 0.3% $KH_2PO_4$ and 0.1% $MgSO_4.7H_2O$ (pH 7.0) was placed in a 500-ml conical flask and sterilized at 120° C. for 20 minutes. Corynebacterium sp. FS-0077(FERM BP-1234) was inoculated to this medium and incubated at 30° C. for 24 hours to give a master culture. Separately, a medium (15 liters) containing 0.1% L-fucose, 0.5% peptone, 0.3% $KH_2PO_4$, 0.1% $MgSO_4.7H_2O$ and 0.01%(v/v) of a defoamer (CB-442; Nippon Oils & Fats Co., Ltd.) (pH 7.0) was placed in a 30-l jar fermentor and sterilized at 120° C. for 20 minutes. After cooling, 100 ml of the master culture prepared above was added to the fermentor, and cultivation was continued at 30° C. for 40 hours with aeration (15 liters/min) and agitation (250 rpm). The microbial cells were collected by centrifugation, suspended in 500 ml of a 50 mM phosphate buffer (pH 8.0), and broken down by ultrasonic treatment. The resulting mixture was centrifuged, affording 550 ml of supernatant. Its α-L-fucosidase activity was 26.5 units/ml. This supernatant was adsorbed on DEAE-Sepharose CL-6B (Pharmacia) packed in a column (5.0 cm in diameter and 10 cm in length) and previously equilibrated with 50 mM phosphate buffer (pH 8.0), the column was washed with 150 mM phosphate buffer (pH 8.0), and the adsorbed portion was eluted with 300 mM phosphate buffer (pH 8.0) to collect the active fraction. The collected fraction was concentrated and desalted through ultrafiltration, and the concentrate was again adsorbed on DEAE-sepharose packed in a column (2.5 cm in diameter and 10 cm in length) and previously equilibrated with 50 mM phosphate buffer (pH 8.0), and eluted in the same manner as above to collect the active fraction. Sodium chloride was added to the collected fraction so as to give a salt concentration of 4M, and the resulting solution was adsorbed on Phenyl-Sepharose CL-4B (Pharmacia) packed in a column (2.5 cm in diameter and 20 cm in length) and previously equilibrated with 100 mM phosphate buffer containing 4M sodium chloride (pH 8.0). The column was washed with 10 mM phosphate buffer containing 4M sodium chloride (pH 8.0), and the adsorbed portion was eluted with 10 mM phosphate buffer containing 3M sodium chloride to collect the active fraction. The collected fraction was concentrated through a collodion membrane, and the concentrate was subjected to gel filtration through Sepharose CL-6B (Pharmacia) packed in a column (2.5 cm in diameter and 90 cm in length) and previously equilibrated with 100 mM phosphate buffer (pH 8.0). After addition of EDTA as stabilizer to a final concentration of 1 mM, the filtrate was freeze-dried, affording 780 mg of purified enzyme powder. This powder had a relative activity of 9.59 units/mg and showed a single band when measured by disk electrophoresis on polyacrylamide gel.

What we claim is:

1. A method for the quantitative determination of L-fucose in a sample solution, which comprises allowing an L-fucose dehydrogenase derived from Corynebacterium sp. FS-0077 (FERM BP 1234) and having its optimum pH around neutrality to act upon said sample solution in the presence or absence of an α-L-fucosidase, measuring the amount of reduced nicotinamide adenine dinucleotide thus formed and relating the amount of reduced nicotinamide adenine dinucleotide measured to the amount of L-fucose in the sample.

2. The method as defined in claim 1, wherein said L-fucose in the sample solution is free L-fucose and/or L-fucose bonded to the glycoconjugates on the surface of cells or glycoconjugates.

3. The method as defined in claim 1, wherein the step of measuring comprises measuring the ultraviolet absorption of the reduced nicotinamide adenine dinucleotide formed.

4. The method as defined in claim 1, wherein the determination of L-fucose is carried out in the presence of reduced nicotinamide adenine dinulceotide, the oxidized form of a tetrazolium salt, and diaphorase or the oxidized form of phenazine methosulfate.

5. A composition for the quantitative determination of L-fucose comprising the following components,
A. an L-fucose dehydrogenase derived from Corynebacterium sp. FS-0077 (FERM BP 1234) and having its optimum pH around neutrality,
B. nicotinamide adenine dinucleotide,
C. the oxidized form of a tetrazolium salt, and
D. diaphorase or the oxidized form of phenazine methosulfate.

* * * * *